United States Patent [19]

van Berkel et al.

[11] Patent Number: 4,544,510

[45] Date of Patent: Oct. 1, 1985

[54] PROCESS FOR PREPARING CYCLOPROPANE CARBOXYLIC ACID ESTER DERIVATIVES

[75] Inventors: Johannes van Berkel; Wilhelmus N. Ruyters, both of Amsterdam, Netherlands

[73] Assignee: Shell Internationale Research Maatschappij B.V., The Hague, Netherlands

[21] Appl. No.: 545,302

[22] Filed: Oct. 25, 1983

[30] Foreign Application Priority Data

Nov. 11, 1982 [GB] United Kingdom ............ 8232283

[51] Int. Cl.$^4$ .......................................... C07C 121/75
[52] U.S. Cl. ................................................ 260/465 D
[58] Field of Search .................................... 260/465 D

[56] References Cited

U.S. PATENT DOCUMENTS

| 4,308,279 | 12/1981 | Smeltz | 424/304 |
| 4,427,598 | 1/1984 | Mason et al. | 260/465 D |
| 4,436,667 | 3/1984 | Bull | 260/465 D |

*Primary Examiner*—Dolph H. Torrence

[57] ABSTRACT

A process for preparing a compound according to formula I containing substantially equimolar amounts of the 1R cis S- and the 1S cis R-isomers (the cis-2 enantiomer pair) and substantially free of the 1R cis R- and the 1S cis S-isomers (the cis-1 enantiomer pair),

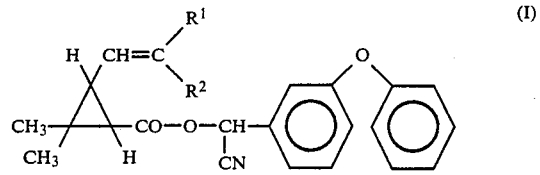

wherein $R^1$ and $R^2$ are each independently selected from chlorine, bromine and methyl, which process comprises contacting the cis-1 enantiomer pair, alone or in the presence of the cis-2 enantiomer pair, with an organic amine base containing from 5 to 7 carbon atoms and being a secondary amine containing two branched alkyl groups or being a tertiary amine, and then separating off a solid compound containing the cis-2 enantiomer pair and substantially free of the cis-1 enantiomer pair, characterized in that the reaction mixture is in the form of a solid-liquid slurry.

10 Claims, No Drawings

PROCESS FOR PREPARING CYCLOPROPANE CARBOXYLIC ACID ESTER DERIVATIVES

This application relates to the preparation of pesticidal cyclopropane carboxylic acid ester derivatives.

Cyclopropane carboxylic acid ester derivatives of general formula

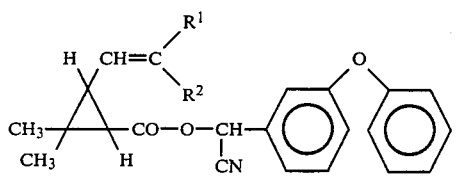
(I)

wherein $R^1$ and $R^2$ are independently selected from chlorine, bromine and methyl, are known compounds haaving pesticidal activity, see for example UK Patent Specification No. 1,413,491 or U.S. Pat. No. 4,024,163. These derivatives are members of a class of pesticidal compounds commonly referred to in the art as pyrethroid insecticides. Compounds of formula I contain two centres of asymmetry in the cyclopropane ring of the acid moiety and a third centre of asymmetry in the alcohol moiety, leading to the existence of eight possible isomers, or even sixteen, if $R^1 \neq R^2$. In general, superior pesticidal activity resides among the compounds having cis-configuration about the cyclopropane ring, as disclosed by Itaya et al. in "Synthetic Pyrethroids", ACS Symposium Series 42, pages 45 to 54, and the isomer which has the greatest pesticidal activity is generally that isomer which is conveniently designated the 1R cis S isomer, 1R cis designating configuration in the acid moiety and S designating configuration in the alcohol moiety, as described by Elliott et al. in Nature, Vol. 248, pages 710 and 711 (1974).

UK Patent Application No. 8112344 (U.S. Pat. No. 2,075,011) describes and claims a process for preparing a compound of formula I in the form of a 1:1 mixture of the 1R cis S- and 1S cis R-isomers (the cis-2 enantiomer pair) substantially free of 1S cis S- and 1R cis R-isomers (the cis-1 enantiomer pair), which process comprises dissolving the cis-1 enantiomer pair, alone or in the presence of the cis-2 enantiomer pair, in an organic amine base containing from 5 to 7 carbon atoms and being a secondary amine containing two branched alkyl groups or being a tertiary amine, and crystallising out from the resulting solution of cis-isomers of formula I in the amine base the cis-2 enantiomer pair substantially free of the cis-1 enantiomer pair. A similar process is described and claimed in UK Patent Application No. 8112325 (U.S. Pat No. 2,074,573). The Applicants had made the surprising discovery that the organic amine bases which may be used in the processes of the cited applications not only have the property of causing epimerisation at the α-carbon atom of the alcohol moiety of the compound of formula I but are also solvents from which the cis-2 enantiomer pair of the isomers of formula I crystallizes faster than the cis-1 enantiomer pair.

In the processes of the cited applications, as the cis-2 enantiomer pair crystallises out from the solution of cis-isomers, the solution tends to become relatively depleted in the isomer comprising the cis-2 enantiomer pair. This tendency is counter-balanced by the effect of the organic amine base in causing the epimerisation of the isomers comprising the cis-1 enantiomer pair to the isomers comprising the cis-2 enantiomer pair. Thus as the cis-2 enantiomer pair is removed from solution by crystallisation, further quantities of the cis-2 enantiomer pair are formed by epimerisation, which process continues until a final equilibrium is attained.

Although both cited processes are very satisfactory from a practical and economic point of view, a special embodiment thereof has now been found which unexpectedly gives especially useful results. The improvement is based on the surprising finding that first completely dissolving the whole of the starting mixture of isomers—as was the preferred way of carrying out the two cited processes—is not required to obtain an essentially pure, crystalline cis-2 enantiomer pair. Instead of a homogeneous liquid system a solid-liquid slurry may be present from the start of the process.

The invention therefore provides a process for preparing a compound according to formula I containing substantially equimolar amounts of the 1R cis S- and the 1S cis R-isomers (the cis-2 enantiomer pair) and substantially free of the 1R cis R- and the 1S cis S-isomers (the cis-1 enantiomer pair),

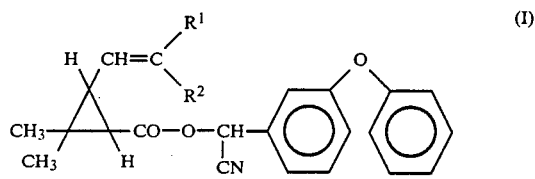
(I)

wherein $R^1$ and $R^2$ are each independently selected from chlorine, bromine and methyl, which process comprises contacting the cis-1 enantiomer pair, alone or in the presence of the cis-2 enantiomer pair, with an organic amine base containing 5 to 7 carbon atoms and being a secondary amine containing two branched alkyl groups or being a tertiary amine, and then separating off a solid compound containing the cis-2 enantiomer pair and substantially free of the cis-1 enantiomer pair, characterized in that the reaction mixture is in the form of a solid-liquid slurry.

It is preferred that $R^1$ and $R^2$ are both chlorine or bromine atoms, and they are preferably both chlorine atoms.

The surprising effect of the invention is that the solid which is finally collected, is an essentially pure cis-2 enantiomer pair. In other words, if one were able to cut in two the crystals finally present, one would find that these do not consist of a core containing cis-1 enantiomer pair covered with a layer of cis-2 enantiomer pair, but are homogeneously pure.

As the starting material is usually partly or wholly crystalline, in order to ensure complete dissolution of the 1S cis S- and 1R cis R-isomers of the compound of formula I, it was preferred formerly to dissolve the mixture of isomers of formula I in the organic amine base at elevated temperature, e.g. a temperature in the range 50° to 80° C. However, in the process of the invention, such heating is not necessary and the mixture of isomers of formula I may advantageously be added to the organic amine base at lower temperatures, especially ambient temperature. Thus energy is saved and, more importantly, undesired side-reactions, such as cis-trans isomerizations, are less likely to occur. This results in a better purity both of the product and the amine base, so that the amine base can be re-used more times, if desired.

The present invention enables the process to be carried out with far less organic amine base than hitherto preferred. Advantageously the slurry contains from 0.1 to 4 g organic amine base per g of total cis-isomers of the compound of formula I, in particular from 0.7 to 2 g. Since the solubility is greater at higher temperatures, less amine base should be employed than is possible at low temperatures, in order to prevent the slurry from becoming a solution.

By consecutively using the mother liquor obtained in one reaction in a following reaction, high yields can be obtained, without concentrating filtrates as preferred in prior art processes. In the present process, moreover, the amine base can be re-used more often since less decomposition products will build up, due to the lower process temperatures.

Although the presence of small amounts of water in the organic amine base may be tolerated, the amount of water should preferably be less than 1% by weight of the base, advantageously less than 0.2%. Further, the presence of solvents which would dissolve the cis-isomers is undesirable, as this would change the slurry into a solution.

The contacting may be effected at any temperature at which the slurry is stable, bearing in mind that at higher temperatures the solubility increases, and the epimerisation rate of the α-carbon of the alcohol portion too, but that—on the other hand—the rates of undesired side reactions, e.g. cis-trans isomerization, increase as well. Preferably the contacting is carried out at a temperature in the range of −10° to 50° C., particularly 15° to 25° C. and most advantageously at ambient temperature. The reaction time should be adequate to ensure that the desired yield of a product of adequate purity is obtained; this contact time will be dependent on the reaction temperature, inter alia, and generally lies between 1 and 240 hours. The adequate period of time may have to be 72, or even 240, hours at low temperatures, whereas at 30° to 40° C. a few hours will suffice. At the most preferred temperature range of 15° to 25° C., the contact time preferably varies from 12 to 48 hours.

The preferred organic amine bases contain six carbon atoms. Triethylamine and diisopropylamine and suitable organic amine bases, and triethylamine is particularly preferred.

The contacting is preferably enhanced by agitation, such as stirring or shaking, or by forced circulation of the supernatant liquid through a filtercake.

Recovering of the crystalline cis-2 enantiomer pair from the supernatant slurry liquid may be effected by methods such as filtration, centrifugation or decantation.

The remaining solution may then be concentrated, or additional amounts of the cis-isomers of the compound of formula I may be added thereto, and further contacting may be effected with the resulting slurry.

It will be appreciated that the most readily available starting material for the process of the invention will be an approximately equimolar mixture of all four cis-isomers of the compound of formula I, although the process is equally applicable to starting materials containing unequal mixtures of cis-isomers. Thus the process of the invention also has the advantages that it yields a product which contains a high proportion of the most pesticidally-active isomer of the relevant compound of formula I and that it does not involve any asymmetric synthesis or optical resolution steps.

The invention also extends to the compound according to formula I containing substantially equimolar amounts of the 1R cis S- and the 1S cis R-isomers and substantially free of the 1R cis R- and the 1S cis S-isomers whenever prepared by the process of the invention, to a pesticidal composition comprising the said compound in association with a suitable carrier, and to a method of combating pests at a locus which comprises applying to the locus the said compound or a composition containing the said compound. The constitution of suitable pesticidal compositions is described in the afore-mentioned UK Patent Specification No. 1,413,491.

The following Examples illustrate the invention.

EXAMPLE 1

In a 0.5 liter reactor were placed 154.3 g of crystalline, nearly pure cis-cypermethrin (a roughly equimolar mixture of the four cis-isomers of α-cyano-3-phenoxybenzyl 3-(2,2-dichlorovinyl)-2,2-dimethylcyclopropane carboxylate), containing 98.4% by weight of cypermethrin and having a cis-trans ratio of 98.1:1.9, and 153.1 g of triethylamine. After stirring the resulting slurry for 24 hours, at 20° C., the crystals were separated off by filtration, washed with 2×50 ml n-hexane and dried in a vacuum oven for 3 hours at 40° C., to give 102.4 g of crystals. Analysis by gas chromatography and by high pressure liquid chromatography showed these crystals to contain 98.3% by weight of cypermethrin, having a cis-trans ratio of 100:0, and a cis 2:cis 1 ratio of 97.7:2.3. This corresponds to an isolated yield of the cis-2 enantiomer pair of 66.0%.

EXAMPLE 2

The process of Example 1 was repeated except that the slurry was stirred at 20° C. for 5 days instead of 24 hours. The resulting isolated yield of cis-2 enantiomer pair was 72.5%.

EXAMPLE 3

To 205 g of an almost saturated triethylamine mother liquor obtained from a previous crystallization experiment, containing 24.8% w of cypermethrin having a cis-trans ratio of 90.1:9.9 in a 0.5 l reactor, 100.0 g crystalline, nearly pure cis-cypermethrin was added. The cis-cypermethrin added had a cypermethrin content of 98.9% w, a cis-trans ratio of 97.6:2.4 and a cis 2:cis 1 ratio of 45:55. The resulting slurry was stirred for 24 hours, and the crystals were separated off and purified as in Example 1. 91.1 g dry crystals were obtained, the analysis of which was 98.8% w cypermethrin, cis-trans ratio 99.3:0.7, and cis 2:cis 1 ratio 97.9:2.1. The yield, calculated as (cis-2 enantiomer pair in product crystals: cis-cypermethrin in crystals added to the triethylamine mother liquor)×100% was 90.6%.

The mother liquor was replenished with triethylamine to 204 g in order to compensate for the small losses of amine. It then had a cypermethrin content of 24.3% w with a cis-trans ratio of 87.5:12.5 and was available for use in a subsequent experiment.

EXAMPLE 4

The process of Example 1 was repeated except that instead of the crystalline, technical material used as starting material, a crude sample of cis-cypermethrin was used. This contained 90% by weight of cypermethrin having a cis:trans ratio of 97.5:2.5 and 10% n-heptane. The resulting isolated yield of cis-2 enantiomer pair was 61%.

EXAMPLE 5

For comparative purposes an experiment was carried out according to the preferred embodiment of UK Patent Application No. 8112344 using 223 g i.e. an excess, of triethyl amine and heating the components to 70° C. in order to dissolve all solid material, but all other conditions being as in Example 1 above. The solution was allowed to cool to ambient temperature. After stirring for 58 hours and separation and washing as above, analysis showed the resulting crystals to weigh 77.42 g, and to have a cis-trans ratio of 97.5:2.5, and a cis 2:cis 1 ratio of 97.4:2.6. Thus from 148.95 g of pure cis-cypermethrin 73.55 g of the cis-2 enantiomer pair was obtained, corresponding to an isolated yield of 49.4%.

Thus the process of the invention results in both a higher yield and a higher purity, in a shorter time.

We claim:

1. A process for preparing a compound according to formula I containing substantially equimolar amounts of the 1R cis S- and the 1S cis R-isomers (the cis-2 enantiomer pair) and substantially free of the 1R cis R- and the 1S cis S-isomers (the cis-1 enantiomer pair),

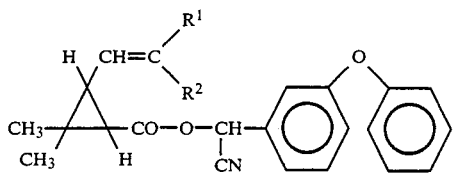

(I)

wherein $R^1$ and $R^2$ are each independently selected from chlorine, bromine and methyl, which process comprises contacting the cis-1 enantiomer pair, alone or in the presence of the cis-2 enantiomer pair, with an organic amine base containing from 5 to 7 carbon atoms and being a secondary amine containing two branched alkyl groups or being a tertiary amine, and then separating off a solid compound containing the cis-2 enantiomer pair and substantially free of the cis-1 enantiomer pair, characterized in that the reaction mixture is in the form of a solid-liquid slurry.

2. A process as claimed in claim 1, characterized in that the slurry contains from 0.1 to 4 g organic amine base per g of total cis-isomers of the compound of formula I.

3. A process as claimed in claim 1 or claim 2, characterized in that the slurry contains less than 1% by weight of water, based on the weight of amine.

4. A process as claimed in claim 3, characterized in that the contacting is carried out at a temperature in the range of $-10°$ to 50° C.

5. A process as claimed in claim 4, characterized in that the organic amine base is triethylamine.

6. A process as claimed in claim 5, in which $R^1$ and $R^2$ are both chlorine atoms.

7. A process as claimed in claim 6, in which the contacting is carried out in the absence of solvents which would dissolve the cis-isomers.

8. A process as claimed in claim 7, in which the contacting is carried out at a temperature in the range of 15° to 25° C.

9. A process as claimed in claim 3, in which the contacting is carried out in the absence of solvents which would dissolve the cis-isomers.

10. A process as claimed in claim 3, in which the contacting is carried out at a temperature in the range of 15° to 25° C.

* * * * *